(12) United States Patent
Nieendick et al.

(10) Patent No.: US 12,274,770 B2
(45) Date of Patent: Apr. 15, 2025

(54) STABILIZER CONCENTRATES FOR WAX DISPERSIONS

(71) Applicant: BASF SE, Ludwigshafen (DE)

(72) Inventors: Claus Nieendick, Düsseldorf-Holthausen (DE); Werner Mauer, Düsseldorf-Holthausen (DE); Kathrin Tapp, Düsseldorf-Holthausen (DE); Sybille Cornelsen, Monheim (DE)

(73) Assignee: BASF SE, Ludwigshafen (DE)

( * ) Notice: Subject to any disclaimer, the term of this patent is extended or adjusted under 35 U.S.C. 154(b) by 728 days.

(21) Appl. No.: 17/434,776

(22) PCT Filed: Mar. 10, 2020

(86) PCT No.: PCT/EP2020/056291
§ 371 (c)(1),
(2) Date: Aug. 30, 2021

(87) PCT Pub. No.: WO2020/182784
PCT Pub. Date: Sep. 17, 2020

(65) Prior Publication Data
US 2022/0160592 A1    May 26, 2022

(30) Foreign Application Priority Data
Mar. 13, 2019   (EP) .................................... 19162423

(51) Int. Cl.
| A61K 8/04 | (2006.01) |
| A61K 8/41 | (2006.01) |
| A61K 8/92 | (2006.01) |
| C09K 23/02 | (2022.01) |
| C09K 23/18 | (2022.01) |
| C09K 23/34 | (2022.01) |
| C09K 23/56 | (2022.01) |

(52) U.S. Cl.
CPC .............. *A61K 8/04* (2013.01); *A61K 8/416* (2013.01); *A61K 8/922* (2013.01); *C09K 23/02* (2022.01); *C09K 23/18* (2022.01); *C09K 23/34* (2022.01); *C09K 23/56* (2022.01); *A61K 2800/436* (2013.01); *A61K 2800/52* (2013.01)

(58) Field of Classification Search
CPC ........... A61K 8/04; A61K 8/416; A61K 8/922
See application file for complete search history.

(56) References Cited

U.S. PATENT DOCUMENTS

| 10,835,467 | B2 * | 11/2020 | Schroeder | ................ | A61K 8/86 |
| 2004/0037793 | A1 * | 2/2004 | Nieendick | ................ | A61Q 5/02 |
| | | | | | 424/70.13 |
| 2004/0043045 | A1 | 3/2004 | Seipel et al. | | |
| 2004/0086470 | A1 | 5/2004 | Nieendick et al. | | |
| 2005/0079193 | A1 | 4/2005 | Nieendick et al. | | |
| 2009/0169644 | A1 | 7/2009 | Goddinger et al. | | |

FOREIGN PATENT DOCUMENTS

| CN | 1145026 A | | 3/1997 | | |
| CN | 1190431 A | | 8/1998 | | |
| DE | 2024051 C3 | * | 5/1986 | ............... | A61K 8/86 |
| EP | 0568848 B1 | | 6/1998 | | |
| EP | 0581193 B1 | | 6/1998 | | |
| EP | 1430867 A1 | | 6/2004 | | |
| EP | 1510199 A1 | | 3/2005 | | |
| EP | 2037877 A1 | | 3/2009 | | |
| EP | 3324927 B1 | | 7/2019 | | |
| WO | WO-96/21711 A2 | | 7/1996 | | |
| WO | WO-02/05781 A1 | | 1/2002 | | |
| WO | WO-02/056839 A2 | | 7/2002 | | |
| WO | WO-2003/033634 A1 | | 4/2003 | | |
| WO | WO-2016/064847 A1 | | 4/2016 | | |

OTHER PUBLICATIONS

Krohe, Herman Use of the esterification products of glycerol-ethylene oxide adducts with fatty acids as refatting agents in cosmetic preparations: DE2024051C3 (Year: 1986).*
European Search Report for EP Patent Application No. 19162423.8, Issued on Dec. 19, 2019, 3 pages.
International Application No. PCT/EP2020/056291, International Search Report and Written Opinion, mailed Jun. 9, 2020.
Schwarzkopf & Henkel, "Caring Shower Cream", ID: 6294889, Mintel GNDP, Jan. 2019, 2 pages.

* cited by examiner

*Primary Examiner* — Robert A Wax
*Assistant Examiner* — Andre Mach
(74) *Attorney, Agent, or Firm* — Faegre Drinker Biddle & Reath LLP

(57) ABSTRACT

This invention relates to stabilizer concentrates which improve the stability of mono- and/or diesters of mono- and/or diethylene glycol wax dispersions in personal care compositions, wherein the stabilizer concentrates comprising hydrogenated castor oil and betaines and are free of anionic surfactants.

20 Claims, No Drawings

STABILIZER CONCENTRATES FOR WAX DISPERSIONS

CROSS-REFERENCE TO RELATED APPLICATIONS

This is the U.S. national phase of International Application No. PCT/EP2020/056291, filed Mar. 10, 2020, which claims the benefit of European Patent Application No. 19162423.8, filed on Mar. 13, 2019.

FIELD OF THE INVENTION

This invention relates to stabilizer concentrates which are able to improve the stability of mono- and/or diesters of mono- and/or diethylene glycol wax dispersions, wherein the stabilizer concentrates comprising hydrogenated castor oil and betaines and are free of anionic surfactants; additionally, the invention relates to the use of such concentrates and a process for their production and personal care compositions containing them and a process for the production of the personal care compositions.

PRIOR ART

The use of wax dispersions based on alkylene glycol fatty acid esters is a long-established and known technique for providing personal care products with an attractive, rich and interesting appearance. Depending on the desired appearance properties wax dispersions can be modified to cause pearlizing properties with high brilliance and/or an opacifier properties with a high degree of whiteness. For the intended use in personal care compositions the wax dispersions need to have a high compatibility with other auxiliaries and a good physical stability, especially storage stability is expected. Additionally, the producers of personal care compositions want to have waxes, which are easily to add within the process, without a time and energy consuming production step like melting.

A favourite method is the use of the wax in form of a premixed wax dispersion. European Patents EP 0581193 B1 and EP 0568848 B1 disclose flowable concentrated pearlizing formulations containing large quantities of fatty acid glycol esters, betaines as zwitterionic surfactants and fatty alcohol alkoxylates as nonionic surfactants. The International patent application WO 96/21711 also describes pearlizing concentrates containing nonionic, zwitterionic and anionic surfactants.

WO 2003/033634 A1 discloses opacifier preparations based on fatty acid glycol esters, amphoteric surfactants and fatty acid partial glycerides, which are flowable and high concentrated.

Unfortunately, the use of the wax dispersions in personal care products sometimes leads to separation of the product, which is at least quite aesthetically unattractive to customers. In order to improve the stability of personal care compositions containing wax dispersions EP 2037877 B1 discloses to use hydrogenated castor oil. However, the hydrogenated castor oil needs to be warmed up in an additional manufacturing step, which is slow and costly.

EP 3324927 describes an aqueous dispersion of hydrogenated castor oil, which was used together with a surfactant mixture consisting of anionic, amphoteric and nonionic surfactants to stabilize cosmetic compositions like shampoos or shower gels. The dispersion can be added at room temperature, i.e. no additional manufacturing step is necessary. Nevertheless, these dispersions of hydrogenated castor oil have high viscosities and are not flowable, therefore a long time of stirring with high steering rates is necessary for homogenization.

WO 2016/064847 describes personal care compositions comprising a hydrogenated castor oil premix composition comprising crystals from hydrogenated castor oil formed by combining under high shear hydrogenated castor oil with surfactants and water and heating all up to 65 to 84° C. However, according to all examples the premix compositions need the presence of anionic surfactants and show high viscosities. Additionally, the production of such dispersions is extremely sensitive to temperature variations, and temperatures above 84° C. do not lead to the desired result.

Accordingly, there is a need for further stabilizing agents with high stabilisation effects and a high active content (concentrates), which are flowable and low viscous. Additionally, the stabilizing agents should improve the stability of wax dispersions, which are part of personal care compositions as pearlizing and/or opacifier agents. In addition, the stabilizing concentrates should be able to show stabilizing properties in a wide range of personal care compositions, especially for conditioning compositions, which are difficult to stabilize because of the presence of deposition agents, especially in the presence of cationic polymers. Furthermore, there is a need for stabilizing agents which can be blended in an easy and cost effective manner without any effort, especially at room temperature ("via cold processing").

DESCRIPTION OF THE INVENTION

The invention relates to concentrates for stabilizing wax dispersions comprising waxes selected from the group consisting of mono- and/or diesters of mono- and/or diethylene glycol esters, wherein the concentrates containing
  (a) hydrogenated castor oil,
  (b) surfactants selected from the group consisting of betaines,
  (c) optional nonionic emulsifiers,
  (d) optional other auxiliaries or additives, including salts, and
  (e) water
with the provisos that the concentrates are free from anionic surfactants and the sum of quantities (a) to (d) is in the range from 30% to 80% by weight and add up to 100% by weight by water.

Additionally, the invention relates to a process for the production of concentrates claimed in claim 1, characterized in that the concentrate is prepared by mixing components (a), (b) and optionally (c) and/or optionally (d) together, adding up with the necessary quantity of water, heating the mixture to about 85 to 90° C. and cooling down with agitation.

Additionally, the invention relates to the use of the concentrates as claimed in claim 1 as a stabilizer for wax dispersions comprising waxes selected from the group consisting of mono- and/or diesters of mono- and/or diethylene glycol.

Additionally, the invention relates to personal care compositions comprising
  A) concentrates as claimed in claim 1 and
  B) wax dispersions comprising waxes selected from the group consisting of mono- and/or diesters of mono- and/or diethylene glycol and C) one or more detersive surfactants selected from the groups selected from anionic surfactants, amphoteric or zwitterionic surfactants and D) optional cationic polymers and E) optional other component(s) different from C) and/or D).

And finally the invention relates to a process for the production of personal care compositions as claimed, characterized in that of one or more surfactants C) and the wax dispersion B) and optional cationic polymers D) are mixed at room temperature, and concentrates A) as claimed in at least one of the claims 1 to 10 are added and stirred together; wherein the optionally other components E) can be added before or after the addition of the concentrates A).

It has surprisingly been found that, the avoidance of anionic surfactants in the wax dispersions lead to flowable concentrates with a high content of actives. Additionally, the concentrates according to the invention are very stable themselves and improve very well the stability of wax dispersions comprising fatty acid esters of mono- and or diethylene glycol.

Especially, wax dispersions used as an opacifier in personal care compositions could be improved in their storage stability, i.e. no visual change of white colour and no separation of the personal care products were observed during storage. Surprisingly the effects were also observed in presence of cationic polymers.

According to the invention "concentrates" are compositions with a reduced water content compared to common dispersions, according to the invention the water content is in total preferable between 20 to 70 wt %—based on concentrate.

The abbreviation "wt %" means "weight percentage" and is synonym to "% by weight".

According to the invention "waxes" are compounds having a melting point above 25° C., preferred above 50° C. and especially above 80° C. The melting point was determined according to ISO 6321.

According to the invention the term "free from anionic surfactants" means that no anionic surfactants are added intentionally as a component to prepare the concentrate; therefore, theoretically the concentrate comprises 0 wt % of anionic surfactants; in practice, the components of the concentrates m ay contain by-products, which may also be anionic surfactants. But these potential by-products are not added intentionally and therefore the concentrate is free from anionic surfactants according to the invention.

According to the invention the term "stabilizer for wax dispersion" means that the concentrates stabilize the wax in the dispersion, preferred in the water dispersion, which is part of the personal care composition. The stabilizing effect was measured as storage stability, i.e. the appearance of the wax dispersion or the personal care composition. It should be unchanged for at least 4 weeks at 40° C.

Concentrates

The concentrates according to the invention contain
a) Hydrogenated Castor Oil (HCO)

Castor oil (CAS-Nr. 8001-79-4) is a vegetable oil and contains glycerides, especially triglycerides of fatty acids having C10 to C22 alkyl or alkenyl moieties which incorporate a hydroxyl group. Hydrogenation of castor oil produces hydrogenated castor oil by converting double bonds, which are present in the starting oil as ricinoleyl moieties. These moieties are converted to ricinoleyl moieties, which are saturated hydroxyalkyl moieties, e.g. hydroxystearyl.

The hydrogenated castor oil (HCO) may be processed in any suitable starting form, including, but not limited those selected from solid, molten and mixtures thereof. Useful hydrogenated castor oil (HCO) may have the following characteristics: more than 80 wt %, especially 80-90 wt % triglycerides of ricinoleic acid. The residue may be free fatty acids, water and other impurities.

Preferred are hydrogenated castor oil (HCO) with a melting point of from about 40° C. to about 100° C., alternatively from about 65° C. to about 95° C., and/or Iodine value ranges of from about 0 to about 5, alternatively from about 0 to about 4, and alternatively from about 0 to about 2.6. The melting point of hydrogenated castor oil (HCO) can measured using DSC: Differential Scanning calorimetry.

Suitable hydrogenated castor oil (HCO) include those that are commercially available. Non-limiting examples of commercially available hydrogenated castor oil (HCO) suitable for use include: THIXCIN-R (supplied by Elementis) and Cutina® HR (supplied by BASF Personal Care and Nutrition GmbH), both are supplied as a powder.

Preferred concentrates contain (a) hydrogenated castor oil in the quantity range of from 0.01 to 7% by weight—based on concentrates.

b) Betaine Surfactants

Betaines are known surfactants which are mainly produced by carboxyalkylation, preferably carboxymethylation, of aminic compounds. The starting materials are preferably condensed with halocarboxylic acids or salts thereof, more particularly with sodium chloroacetate. Examples of suitable betaines are the carboxyalkylation products of secondary and, in particular, tertiary amines corresponding to formula (I):

in which $R^1$ stands for alkyl and/or alkenyl groups containing 6 to 22 carbon atoms, $R^2$ stands for hydrogen or alkyl groups containing 1 to 4 carbon atoms, $R^3$ stands for alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Other suitable betaines are carboxyalkylation products of amidoamines corresponding to formula (II):

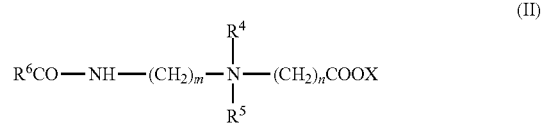

in which $R^6CO$ is an aliphatic acyl group containing 6 to 22 carbon atoms and 0 or 1 to 3 double bonds, m is a number of 1 to 3, $R^4$ represents hydrogen or $C_{1-4}$ alkyl groups, $R^5$ represents $C_{1-4}$ alkyl groups, n is a number of 1 to 6 and X is an alkali metal and/or alkaline earth metal or ammonium. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate known under the CTFA name of Cocamidopropyl Betaine. Betaines distinguished by high purity are particularly preferred; in other words, low-salt betaines with a maximum salt content of 13% by weight, preferably 11% by weight and more particularly 7% by weight—based on active substance—are used. The corresponding salt is dependent on the production of the amphoteric surfactant; in the most common case, it is sodium chloride. In a particularly preferred embodiment, these betaines also have a low content of free fatty acids of at most 4% by weight and preferably at most 3% by weight, based on active substance.

Suitable Cocamidopropyl Betaine include those that are commercially available like Dehyton® PK 45 (supplied by BASF Personal Care and Nutrition GmbH).

Preferred concentrates contain (b) surfactants selected from the group consisting of betaines in the quantity range of from 10 to 45% by weight—based on concentrates.

In a preferred embodiment the quantity ratio of betaines (b) to hydrogenated castor oil (a) is in the range of from 2:1 to 15:1.

c) Optional Nonionic Emulsifiers

According to the invention the concentrates may contain nonionic emulsifiers. In the context of the present invention, the term "nonionic surfactant" or "nonionic emulsifiers" are used synonymous and it is also understood to mean a mixture of two or more.

Examples for nonionic emulsifiers are fatty alcohol polyglycol ether; alkylphenol polyglycol ether; fatty acid polyglycol ester; fatty acid amide polyglycol ether; fatty amine polyglycol ether; optionally alkoxylated polyol fatty acid ester, in particular ethoxylated fatty acid glycerol ester; alkoxylated triglycerides; mixed ethers or mixed formals; optionally partially oxidized alk(en)yl polyglycosides or glucuronic acid derivatives; fatty acid N-alkylglucamides; protein hydrolysates (in particular wheat-based plant products); polysorbates and amine oxides.

If the nonionic emulsifiers contain polyglycol ether chains, these may have a conventional homolog distribution, but preferably have a narrow homolog distribution.

Preferred examples for optionally alkoxylated polyol fatty acid esters may be selected from the following groups of compounds- with the provisio that (c) is different from (a):

partial esters of glycerol and/or sorbitan with unsaturated, linear or saturated, linear or branched fatty acids containing 6 to 22 carbon atoms and/or hydroxycarboxylic acids containing 3 to 18 carbon atoms and adducts thereof with 1 to 30 mol ethylene oxide;

partial esters of polyglycerol (average degree of self-condensation 2 to 8), polyethylene glycol (molecular weight 400 to 5.000), trimethylolpropane, pentaerythritol, sugar alcohols (for example sorbitol), with saturated and/or unsaturated, linear or branched fatty acids containing 6 to 22 carbon atoms and/or hydroxycarboxylic acids containing 3 to 18 carbon atoms and adducts thereof with 1 to 30 mol ethylene oxide;

mixed esters of pentaerythritol, fatty acids, citric acid and fatty alcohol and/or mixed esters of fatty acids containing 6 to 22 carbon atoms, methyl glucose and polyols, preferably glycerol or polyglycerol.

Typical examples of suitable partial glycerides are the following, which are different from (a), hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof.

Examples of other suitable polyolester are the mono-, di- and triester of trimethylol propane or pentaerythritol with lauric acid, coco fatty acid, tallow fatty acid, palmitic acid, stearic acid, oleic acid, behenic acid and the like optionally reacted with 1 to 30 mol ethylene oxide.

Within the optionally alkoxylated fatty acid glycerol esters preference is given to nonionic emulsifiers to partial esters of ethoxylated glycerol, in particular wherein the monoester content in the mixture of mono, di- and triester is more than 40% by weight. Suitable is the commercial product Cetiol® HE, available by BASF Personal Care Nutrition GmbH.

Additionally, alkyl polyglycosides are preferred nonionic emulsifiers and known nonionic surfactants which have in particular the formula (III), $$R^7O\text{-}[G]_p \qquad (III)$$

in which

R⁷ is an alkyl radical having 6 to 22 carbon atoms,
G is a sugar radical having five or six carbon atoms and
p is a number from 1 to 10.

They can be obtained by the relevant methods of preparative organic chemistry. The alkyl polyglycosides can be derived from aldoses or ketoses having 5 or 6 carbon atoms, preferably from glucose. The preferred alkyl polyglycosides are therefore alkyl polyglucosides. The index number p in the general formula (III) specifies the degree of polymerization (DP), i.e. the distribution of mono- and polyglycosides, and is a number between 1 and 10. Whereas p in a given compound must always be an integer and can here in particular assume the values p =1 to 6, the value p for a particular alkyl polyglycoside is an analytically determined calculated parameter which in most cases is a fraction. Preferably, alkyl polyglycosides are used with an average degree of polymerization p of 1.1 to 3.0. Preference is given to those alkyl polyglycosides, from a technical applications point of view, for which the degree of polymerization is less than 1.7 and is particularly between 1.2 and 1.7.

The alkyl radical R⁷ can be derived from primary alcohols having 6 to 22, preferably 6 to 18 carbon atoms. Typical examples are caproic alcohol, caprylic alcohol, capric alcohol, decyl alcohol and undecyl alcohol, and also their technical grade mixtures, as obtained, for example, in the hydrogenation of technical grade fatty acid methyl esters or during the hydrogenation of aldehydes from Roelen's oxo synthesis. The alkyl radical R⁷ can also be derived from lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and also technical grade mixtures thereof.

In the context of the present invention, preference is given in particular to mixtures of different alkyl polyglycosides of the formula (III), in which R⁷ is derived from primary alcohol mixtures. According to one preference R⁷ is derived from primary alcohol mixtures comprising 10 to 50% by weight 8 and 10 carbon atoms and 50 to 90% by weight 12 to 16 carbon atoms.

According to another preference R⁷ is derived from primary alcohol mixtures comprising 75 to 95% by weight primary higher alcohols with 10 to 22 carbon atoms, especially derivated from fatty acid mixture obtained from coco nut, preferably 12 to 16 carbon atoms.

Suitable products are Plantacare® 2000 and Plantacare® 818, both available by BASF Personal Care Nutrition GmbH.

Preferably the concentrates contain the nonionic emulsifiers (c) selected from the group consisting of partial esters of glycerol with saturated and/or unsaturated linear fatty acids containing 6 to 22 carbon atoms and adducts thereof with 1 to 30 mol ethylene oxide and alkyl poly glucosides with saturated and/or unsaturated, linear or branched fatty acids containing 6 to 22 carbon atoms.

Preferably the concentrates contain the nonionic emulsifiers (c) in the quantity range of from 0 to 30% by weight, preferred 5.0 to 30% by weight—based on concentrates.

Optional Other Auxiliaries or Additives, Including Salts d)

According to the invention the concentrates may contain d) other auxiliaries or additives, including salts.

Dependent on the production of the betain surfactant (b) salts may be contained as a by-product; in the most common cases, it is sodium chloride. Additionally, a low content of free fatty acids may be a possible by-product.

Examples for other auxiliaries are thickeners, complexing agents, nonaqueous solvents, preservatives and/or pH-adjusters. It is preferred not to add any auxiliaries, but it is still possible.

Preferred concentrates contain other auxiliaries or additives, including salts, (d) in the quantity range of from 0.1 to 15% by weight, based on concentrates substance.

According to one preferred embodiment the concentrates consist of (a) 0.5 to 7.0% by weight of hydrogenated castor oil,
(b) 30.0 to 40.0% by weight of surfactants selected from the group consisting of betaines,
(d) 5.0 to 10.0% by weight of other auxiliaries or additives, including salts, and
(e) add up to 100% by weight by water.

According to another preferred embodiment the concentrates consist of (a) 0.5 to 7.0% by weight of hydrogenated castor oil,
(b) 10 to 35.0% by weight of surfactants selected from the group consisting of betaines,
(c) 5.0 to 30.0% by weight of nonionic emulsifiers,
(d) 2.0 to 10.0% by weight of other auxiliaries or additives, including salts, and
(e) add up to 100% by weight by water.

According to the invention the concentrates are flowable and have a viscosity (Brookfield, RVT; spindle 4; 10 rpm; 23) in the range of from 8.000 to 25.000 mPas, especially 9.000 to 20.000 mPas.

According to the invention the concentrate can be obtained by the following process: the concentrate is prepared by mixing components (a), (b) and optionally (c) and/or optionally (d) together, adding up with the necessary quantity of water and heating the mixture to about 85 to 95° C. before cooling down with agitation. It is preferred to heat the mixture to about 88-93° C. It is preferred to cool the reaction mixture down with agitation, for example with stirring, especially at least 5 to 150 minutes and preferred with 50-150 rpm. In the sense of the invention it is desired to avoid crystallization or recrystallization of the hydrogenated castor oil (a) during the process. For cooling a cooling rate of 15-30° C. per hour is preferred during the process.

According to the invention the concentrates are used as a stabilizer for wax dispersions comprising waxes selected from the group consisting of mono- and/or diesters of mono- and/or diethylene glycol.

Stabilized Wax Dispersions

According to the inventions all wax dispersions comprise one or more waxes selected from the group consisting of mono- and/or diesters of mono- and/or diethylene glycol.

According to the invention the term "mono- and/or diesters of mono- and/or diesters of diethylene glycol" means monoesters of mono ethylene glycol, monoesters of diethylene glycol and diesters of diethylene glycol and their mixtures.

The following formula describes suitable esters of ethylene glycol:

$$R^8CO(OA)_qOR^9 \qquad (IV)$$

in which R⁸CO is a linear or branched, saturated or unsaturated acyl group containing 6 to 22 carbon atoms, R⁹ is hydrogen or has the same meaning as R⁸CO and A is a linear alkylene group containing 2 carbon atoms and q is a number of 2, provided that they are waxes at room temperature. Typical examples are monoesters of mono ethylene glycol and mono- and/or diesters of diethylene glycol (q=2) with fatty acids containing 16 to 22 and preferably 16 to 18 carbon atoms, such as palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof.

Preferred are mono- and/or diesters of diethylene glycol, especially with fatty acids with 6-22 carbon atoms.

According to one embodiment of the invention the stabilized wax dispersion comprises mono- and/or diesters of diethylene glycol with $C_{16}$- to $C_{18}$-fatty acid mixtures, preferably stearic acid, palmitic acid and mixtures thereof. In particular, a mixture is preferred and the ratio in the mixture of palmitic acid to stearic acid is preferably from 45:55 to 1:99, more preferably from 40:60 to 1:99, more preferably still from 30:70 to 1:99, more preferably still from 30:70 to 2:98.

According to a second embodiment of the invention the stabilized wax dispersion comprises mono- and/or diesters of diethylene glycol with a fatty acid mixture containing 85 to 100 wt % stearic acid and 0 to 15 wt % different fatty acids with 12 to 22 carbon atoms—based on the total amount of fatty acid. The fatty acid mixture preferably contains 90 to 98 wt % stearic acid and 2 to 10 wt % other saturated fatty acids with 16 to 22 carbon atoms—based on the total amount of fatty acid—and in particular the fatty acid mixture consists of 90 to 96 wt % stearic acid and 4 to 10 wt % other saturated fatty acids with 16 to 22 carbon atoms. Other saturated fatty acids with 16 to 22 carbon atoms are palmitic acid, arachidic acid and behenic acid.

Preferably the stabilized wax dispersion comprises diethylene glycol fatty acid esters, especially diethylene glycol difatty acid esters which, for technical reasons, contain 90 to 100 wt % diethylene glycol diacid esters and 0 to 10% by weight of diethylene glycol mono fatty acid esters.

In a very particularly preferred embodiment the concentrates according to the invention stabilizes wax dispersions, wherein the wax is a diester of diethylene glycol fatty acid ester with 90 to 100 wt % diethylene glycol difatty acid content and 90 to 98 wt % stearic acid and 2 to 10 wt % other saturated fatty acids with 16 to 22 carbon atoms content in the fatty acid mixture.

Such a product is available on the market under the brand name Cutina® KE 2747, BASF.

According to the particular preferred embodiment the wax in the dispersions have an average particle diameter in the range of 0.8 to 3.5 μm, especially in the range of 1.0 to 3.0 μm, wherein the distribution of the particle diameters shows preferable more than 50% are below 3 μm and 90% of all particles are below 7 μm. In particular, the wax particle have predominantly spherical particle shapes, especially 70% of all particles having a three-dimensional structure which is characterized in particular by a ratio of height: width: length of 1:1:1. Such particle shapes and particle quantities can be determined by laser diffraction with the Mastersizer® 2000 device and the corresponding product description of MALVERN INSTRUMENTS GmbH, Marie-Curie-Straße 4/1, 71083 Herrenberg, Germany.

Preferably the wax dispersions contain the wax in quantities of 20 to 35 wt %, preferably 25 to 30% by weight, based on the wax dispersion.

Preferably the wax dispersions contain nonionic surfactants as a further component. Suitable are the nonionic surfactants, which have been already described as an ingredient of the concentrates according to the invention or which are described as an ingredient of the personal care compositions. Preferred nonionic surfactants are fatty acid partial glycerides. In this context fatty acid partial glycerides means monoglycerides, diglycerides and their technical mixtures, which may still contain small amounts of glycerol and triglycerides due to the manufacturing process. Preferred fatty acid partial glycerides are technical mixtures of fatty acid partial glycerides which have a monoglyceride content in the range of 50 to 95 wt %, preferably 60 to 90 wt %, and are hereinafter also referred to as glycerol mono fatty acid esters.

Preferred fatty acid partial glycerides are selected from the group formed by the glycerol mono-fatty acid ester, with lauric acid, isotridecanoic acid, myristinic acid, palmitic acid, palmoleic acid, stearic acid, isostearic acid, oleic acid, elaidic acid, petroselinic acid, linol acid, linolenic acid, elaeo-stearic acid, arachinic acid, gadoleic acid, behenic acid and erucic acid as well as their technical mixtures. Particularly preferred are mono fatty acid esters of (technical) glycerol and of fatty acids having 12 to 18 C atoms, preferably of a fatty acid mixture which contains 90 to 100% by weight of oleic acid—based on fatty acid mixture.

A suitable technical product on the market, for example, is Monomuls® 90-O 18, a retail product of BASF Personal Care & Nutrition GmbH.

The nonionic surfactants, especially fatty acid partial glycerides, are preferably contained in quantities of 0.5 to 3.0, preferably 1.0 to 2% by weight, based on the wax dispersion.

The wax dispersions may additionally contain anionic surfactants selected from the group consisting of fatty alcohol (ether) sulfates.

In particular, fatty alcohol (ether) sulfates of the general formula (V), $$R'O(CH_2CH_2O)_{0-10}SO_3Y \qquad (V)$$

in which R" is a linear or branched alkyl and/or alkenyl radical having 6 to 22 carbon atoms and Y is an alkali metal and/or alkaline earth metal, ammonium, alkylammonium, alkanolammonium or glucammonium. If the number is zero (=0), this is fatty alcohol sulphate. Fatty alcohol ether sulphates (number from 1 to 10) are preferred. Typical examples are the sulphates of investment products of on average 1 to 10 and in particular 2 to 5 mol ethylene oxide of capron alcohol, capryl alcohol, 2-ethylhexyl alcohol, capri alcohol, lauryl alcohol, isotridecyl alcohol, myristyl alcohol, cetyl alcohol, Palmoleyl alcohol, stearyl alcohol, isostearyl alcohol, ( )eyl alcohol, elaidyl alcohol, petroselinyl alcohol, arachyl alcohol, gadoleyl alcohol, behenyl alcohol, erucyl alcohol and brassidyl alcohol and their technical mixtures in the form of their sodium and/or magnesium salts. The fatty alcohol (ether) sulfates may have both a conventional and a narrowed homologue distribution. It is particularly preferred to use fatty alcohol ether sulfates based on adducts of, on average, 1 to 6 mol and preferably 1 to 3 mol ethylene oxide with lauryl ether sulfate, preferably with technical $C_{12/14}$,  or $C_{12/18}$ coconut fatty alcohol fractions in the form of their sodium and/or magnesium salts.

A suitable technical product on the market, for example, is Texapon® N70, a retail product of BASF Personal Care & Nutrition GmbH.

Preferred wax dispersions contain anionic surfactants, especially lauryl ether sulphate with an average degree of ethoxylation of 1 or 2, preferably in an amount of 8 to 15, preferably 9 to 12 wt %—based on wax dispersion.

Additionally the wax dispersions may contain betaine surfactants, which have been already described as component b) of the inventive concentrate, preferably betaine surfactants according to formula (I) and/or (II) and in particular according to formula (II), and within this group it is preferred to use a condensation product of $C_{8/18}$ coco fatty acid-N,N-dimethyl aminopropyl amide with sodium chloroacetate known under the CTFA name of Cocamidopropyl Betaine.

Preferred wax dispersions contain betaine surfactants, especially Cocamidopropyl Betaine, preferably in an amount of 0 to 5, preferably 0.5 to 2.5 wt %—based on wax dispersion.

It may possible that the dispersions contain additionally auxiliaries or additives, including salts, which have been for example described as component d) in the concentrates, preferably in an amount of 0 to 10 wt %.

In the end the wax dispersions contain up to 100 wt % water.

According to the invention it is preferred that the concentrates are used as a stabilizer for wax dispersions comprising—wt % based on the wax dispersion—

20 to 35 wt %, preferably 25 to 30 wt %, waxes selected from the group consisting of mono- and/or diesters of mono- and/or diethylene glycol, and 0.5 to 3.0 wt %, preferably 1.0 to 2 wt %, nonionic surfactants and 8.0 to 15.0 wt %, preferably 9.0 to 12.0 wt %, anionic surfactants and 0 to 5.0 wt %, preferably 0.5 to 2.5 wt %, betaine surfactants and 0 to 10 wt % auxiliaries or additives, including salts, and up to 100 wt % water.

In particular, for wax dispersions consisting of 20 to 35 wt %, preferably 25 to 30 wt %, waxes selected from diester of diethylene glycol fatty acid ester with 90 to 100 wt % diethylene glycol difatty acid content and 90 to 98 wt % stearic acid and 2 to 10 wt % other saturated fatty acids with 16 to 22 carbon atoms content in the fatty acid mixture, and 0.5 to 3.0 wt %, preferably 1.0 to 2 wt %, fatty acid partial glycerides and 8.0 to 15.0 wt %, preferably 9.0 to 12.0 wt %, lauryl ether sulphate with an average degree of ethoxylation of 1 or 2 and 0 to 5.0 wt %, preferably 0.5 to 2.5 wt %, Cocoamidopropyl Betaine, and 0 to 10 wt % auxiliaries or additives, including salts, and up to 100 wt % water.

According to the invention the concentrates stabilize the above described wax dispersions, which are preferably contained in personal care compositions as a pearlizing and/or opacifier agent, particularly in personal care compositions comprising cationic polymers.

Personal Care Compositions

Personal care compositions are to be understood here as all compositions known to a person skilled in the art which are exclusively or primarily intended to be applied externally to the human body or hair for the cleaning, caring, protection, and maintaining of a good condition, perfuming, changing the appearance or for influencing. Preferably the concentrates are used to stabilize the defined wax dispersions in liquid personal care compositions, in particular surface-active personal care compositions, such as, for example, foam baths, shower gels, shower baths, shower milks, shower creams, shampoos, hair masks, hair milks and hair conditioners.

The personal care compositions according to the invention are comprising

A) concentrates as already described and claimed and

B) wax dispersions as already described, comprising waxes selected from the group consisting of mono- and/or diesters of mono- and/or diethylene glycol and C) one or more detersive surfactants selected from the groups selected from anionic surfactants and betaine surfactants and D) optional cationic polymers and E) optional other component(e)s different from C) and/or D).

Preferably the personal care compositions—based on weight % in personal care composition—comprising A) 0.5 wt % to 10.0 wt %, especially 1.5 wt % to 7 wt % of the concentrates as claimed at least in claim 1, B) 0.1 wt % to 5 wt %, especially 0.5 wt % to 2.5 wt % of the wax dispersions already described, C) 1.0 to 30 wt %, especially 5.0 to 25.0 wt % anionic surfactants, amphoteric or zwitterionic surfactants, D) 0 to 5 wt %, especially 0.01 to 1 wt % cationic polymer, E) up to 100 wt % other components, different from C) and/or D).

C) Anionic Surfactants

Examples of anionic surfactants are soaps, alkyl benzenesulfonates, alkane sulfonates, olefin sulfonates, alkyl ether sulfonates, glycerol ether sulfonates, a-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, the polyglycol ether chains may have a conventional homolog distribution, although they preferably have a narrow homolog distribution. Particularly suitable anionic surfactants in the preparations according to the invention are alkyl ether sulfates, which have already been disclosed in formula (V).

Alkyl ether sulfates ("ether sulfates") are known anionic surfactants which, on an industrial scale, are produced by $SO_3$ or chlorosulfonic acid (CSA) sulfation of fatty alcohol or oxoalcohol polyglycol ethers and subsequent neutralization. The ether sulfates may have both a conventional homolog distribution and a narrow homolog distribution. It is particularly preferred to use ether sulfates based on adducts of, on average, 1 to 6 mol and preferably 1 to 3 mol ethylene oxide with technical $C_{12/14}$ or $C_{12/18}$ coconut fatty alcohol fractions in the form of their sodium and/or magnesium salts.

In addition, betaine surfactants may be used in addition with the anionic surfactants. Suitable betaine surfactants have already been described as component b) of the inventive concentrate, preferably betaine surfactants according to formula (I) and/or (II) are useful and in particular according to formula (II). In particular the condensation product of $C_{8/18}$ cocofatty acid-N,N-dimethyl aminopropyl amide with sodium chloroacetate known under the CTFA name of Cocamidopropyl Betaine is preferred.

D) Cationic Polymers

Cationic polymers are known deposition agents, i.e. by using the personal care composition they deposit on skin and/or hair and give them a pleasant and a soft feeling. But personal care compositions containing wax dispersions and cationic guar polymers have problems with their stability and the wax tend to sediment. This problem can be overcome by adding the concentrates according to the invention for stabilization the wax in the personal care composition.

Preferred personal care composition also comprises a cationic polymer. These cationic deposition polymers can include at least one of a cationic guar polymer, a cationic non-guar galactomannan polymer, a cationic tapioca polymer, a cationic copolymer of acrylamide monomers and cationic monomers, and/or a synthetic, non-crosslinked, cationic polymer. Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, JaguarOCBS, Jaguar®C-17, Jaguar®C-16 of Celanese, quaternized ammonium salt polymers such as, for example, Mirapol®A-15, Mirapol® AD-1, Mirapol® AZ-1 of Miranol.

Especially, the personal care composition may comprise cationic polymer selected from the group consisting of cationically modified cellulose derivatives, PQ 10, PQ 67, cationically modified guar derivatives, such as, for example, Dehyquart0 Guar N, guar hydroxypropyltrimonium chloride, cationic homo- or copolymers based on acrylamide, cationic homo- or copolymers based on vinyl pyrrolidone, cationic homo- or copolymers based on quaternized vinyl imidazole and cationic homo- or copolymers based on methacrylates.

In particular, cationically modified guar derivates, preferably Guar Hydroxypropyltrimonium Chloride, are present.

E) Other Components

According to the end application, the cosmetic formulations may comprise a series of further auxiliaries and additives, such as, for example, water, bodying agents, viscosity reducers, thickeners, salts, superfatting agents, stabilizers, polymers, fats, waxes, silicones, lecithins, protein hydrolyates, phospholipids, biogenic active ingredients, UV sunscreen factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, and the like, including water.

For reducing the viscosity, the personal care compositions may additionally contain polyols as an optional component. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1.000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol;

sugars containing 5 to 12 carbon atoms, for example glucose or sucrose;

amino sugars, for example glucamine;

dialcoholamines, such as diethanolamine or 2-aminopropane-1,3-diol.

The polyols are used in quantities of typically 0.1 to 10% by weight, preferably 0.5 to 5% by weight and more particularly 0.7 to 3% by weight, based on the personal care composition. If larger quantities of polyol, preferably glycerol or ethylene glycol, are used, the concentrates are simultaneously stabilized against microbial infestation.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® Iv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers. Salts like sodium chloride can be incorporated as a by-product.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Additionally, film formers may be present. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

If desired, further protein hydrolyzates known from the prior art may be used, for example based on keratin such as the commercially available Nutrilan® Keratin W PP, or based on wheat, such as Gluadin® WLM Benz, Gluadin® WK or Gluadin® WP. It is also possible to add small amounts of free amino acids such as lysine or arginine.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acidand salts and esters thereof, N-(4-chlorophenyl)-N'-(3,4-dichlorophenyl)-urea, 2,4,4'-trichloro-2'-hydroxydiphenylether (triclosan), 4-chloro-3,5-di-methylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, nettle oil, menthol, mint oil, farnesol, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain astringent active agents for example salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohyrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils, synthetic skin-protecting agents and/or oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides. Suitable antidandruff agents are climbazol, octopirox and zinc pyrithione.

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In addition, hydrotropes, for example ethanol, isopropyl alcohol or polyols, may be used to improve flow behavior.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetylaminopropionate. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes which can be used are the substances approved and suitable for cosmetic purposes, as listed, for example, in the publication "Kosmetische Färbemittel" [Cosmetic Colorants] from the Farbstoffkommission der Deutschen Forschungsgemeinschaft [Dyes commission of the German research society], Verlag Chemie, Weinheim, 1984, pp. 81-106. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). As a luminescent dye, it is also possible for luminol to be present. These dyes are usually used in concentrations of from 0.001 to 0.1% by weight, based on the total mixture.

The production of personal care compositions is very easy for the manufactures and time and energy effective as all manufacturing steps can be done at room temperature. As claimed a mixture of one or more surfactants C) and optional cationic polymers D) are prepared by mixing at room temperature, and the inventive concentrates A) are added to the mixture; and optionally other personal care components E) can be added finally. It is also possible to blend at least part of the other components E) with C) and optional D), before adding the inventive concentrates A).

Plantacare® 2000: aqueous solution of C8-C16 fatty alcohol polyglycoside; INCI: Decyl Glucoside; nonionic surfactant Plantacare® 818: aqueous solution of C8-C18 fatty alcohol polyglycoside; INCI Coco-glucoside; nonionic surfactant Texapon® N70: aqueous solution of C12-C14 Alkylethersulfat Na-salt; INCI: Sodium Laureth Sulfate; anionic surfactant; about 70% active matter

TABLE 1

| Concentrate 1 Phase B/ Component A/ Stabilizer | INCI/Ingredients | Product name | 1a % AS by weight | 1b % AS by weight | 1c % AS by weight | 1d % AS by weight | 1e % AS by weight | 1f % AS by weight | 1g % AS by weight | Comparison Example 1 % AS by weight |
|---|---|---|---|---|---|---|---|---|---|---|
| | Cocoamidopropyl Betaine (b) | Cocoamidopropyl Betaine via Dehyton® PK 45 | 36 | 28.5 | 33 | 18 | 10 | 11 | 15 | 31 |
| | Hydrogenated Castor Oil (a) | Cutina® HR Powder | 2.7 | 2.7 | 2.5 | 2.7 | 2.7 | 5.4 | 5.4 | 2.7 |
| | PEG-7 Glyceryl Cocoate (c) | Cetiol® HE | — | 7.7 | 7.7 | — | — | — | — | — |
| | C8-C10- Polyglucoside (c) | Plantacare® 2000 | — | — | — | 18 | — | 28 | — | — |
| | C8-C18 (Coco)-polyglucoside (c) | Plantacare® 818 | — | — | — | — | 28 | — | 25 | — |
| | C12-C14 Alkylethersulfat Na-salt | Texapon® N70 | — | — | — | — | — | — | — | 5 |
| | Sodium chloride (d) | via Dehyton® PK 45 | 7.7 | 6.1 | 7.1 | 3.8 | 2.1 | 2.2 | 3.2 | 6.6 |
| | Sum (a) to (d) | | 46.4 | 45 | 50.3 | 43.5 | 42.8 | 46.6 | 48.6 | 45.3 |
| | Water (e) | via Dehytone PK 45, Plantacare® and/or Texapon® N70) | Up 100 | Up 100 | Up 100 | Up 100 | Up 100 | Up 100 | Up 100 | Up 100 |
| | Weight Ratio (b): (a) | | 13:1 | 10.6:1 | 13:1 | 6.7:1 | 3.7:1 | 2:1 | 2.8:1 | 11.5:1 |
| | Viscosity (Brookfield; RVT; spindle 4; 10 rpm; 23° C.) in mPas | | 16.000 | 11.000 | 14.000 | 10.500 | 4.500 | 16.500 | 20.000 | 145.000; sticky; not flowable |

Table 1 shows that all concentrates without any anionic surfactant are flowable; their viscosity is significantly lower (max. 20.000 mPas) than the viscosity of the concentrate with anionic surfactant (comparison example). The comparison example had a sticky appearance and was not flowable.

EXAMPLES

Example 1: Concentrates with Hydrogenated Castor Oil as Stabilizers (=Component A); Corresponding Phase B) in Personal Care Composition The concentrates were prepared by mixing all compounds listed in the following table 1 in the amount as stated (% weight as active matter) at 90° C. until homogenous and cool down to room temperature (approx. 25° C.) with agitation of 100 rpm for 5-120 minutes.

The following ingredients were used (Active Matter=AS):

Dehyton® PK 45: Cocoamidopropylbetain: with 37% by weight active matter; 7% by weight soda chloride and up to 100% by weight water Cutina® HR Powder: Hydrogenated Castor Oil; 100% by weight active matter Cetiol® HE: nonionic surfactant; mono- and diester of fatty acid mixture based on coconut oil and glycerol, ethoxylated with 7 mol ethylene oxid Example 2: Shower Creams Containing Concentrates According to Example 1 of the Invention The concentrates according to Example 1 of the invention were used to stabilize the following wax dispersion B) (% by weight-based on active matter):

27.0 wt % of a mixture of about 6 wt % of monoester and about 94 wt % of diester of ethylene glycol, wherein the ester building fatty acid had about 90-98.5 wt of C-18 atoms and 2-10 wt C16+C20+C22 carbon atoms (measured with GC; such products are available as Cutina® KE 2747

10.15 wt % Sodium Laureth Sulfate (with 1 EO)

1.73 wt % Cocamidopropyl Betaine 1.55 wt % Glyceryl monooleate up to 100 wt % water, citric acid and benzoate.

The wax dispersion B) is an opacifier and was used in all shower creams in Phase A). The dispersed wax had an average particle size—measured via laser diffraction (Mastersizer 2000®) between 1.5-2.5 μm.

The shower creams were prepared by the following process: All components of Phase A were mixed together and stirred at room temperature (23° C.) until they were completely homogeneous. Phase A) contain as D) the cationic polymer (Dehyquart® Guar N); as C) the surfactants Texapon® N 70 and Dehyton® PK 45 and as B) the above characterized wax dispersion. To Phase A) the inventive, stabilizing concentrate A) according to Example 1 (=Phase B) and afterwards Phase C) was added and stirred until the mixture (personal care composition) was completely homogeneous.

TABLE 2

Personal care compositions

| Example 2 Concentrate | Product name | INCI/active Ingredient | 2a 1a % by weight | 2b 1b % by weight | 2c 1c % by weight | 2d 1d % by weight | 2e 1e % by weight | 2f 1f % by weight | 2g 1g % by weight | Comparison Example 2 Comparison 1 % by weight | Comparison 3 no % by weight |
|---|---|---|---|---|---|---|---|---|---|---|---|
| Phase A) | Water, demin. | Aqua; water demin. | 53.93 | 53.98 | 53.46 | 54.01 | 53.80 | 54.08 | 56.65 | 53.88 | 43.45 |
| | Citric Acid | Citric Acid (50% solut.) | 0.20 | — | — | — | — | — | — | — | 0.20 |
| | Dehyquart ® Guar N (=D)) | Guar Hydroxypropyl-trimonium Chloride | 0.20 | — | — | — | 0.20 | — | — | — | 0.20 |
| | Dehyton ® PK 45 (=C)) | Cocoamidopropyl Betaine | — | — | — | — | — | 2.77 | — | — | 5.40 |
| | Sodium Benzoate | Sodium Benzoate | 0.50 | 0.50 | 0.50 | 0.50 | 0.50 | 0.50 | 0.50 | 0.50 | 0.50 |
| | Texapon ® N 70 (=C)) | Sodium Laureth Sulfate | 14.30 | 14.30 | 14.30 | 14.30 | 14.30 | 14.30 | 14.30 | 14.30 | 14.30 |
| | Wax dispersion (=B)) | Glycol Distearate, Sodium Laureth Sulfate, Cocamidopropyl Betaine, GlycerylOleate | 2.20 | 2.20 | 2.20 | 2.20 | 2.20 | 2.20 | 2.20 | 2.20 | 2.20 |
| Phase B) | Concentrates A); see Table 1 | | 5.55 | 5.55 | 6.00 | 5.55 | 5.55 | 2.78 | 2.78 | 5.55 | — |
| Phase C) | Water, demin. | Aqua | 20.00 | 20.00 | 20.00 | 20.00 | 20.00 | 20.00 | 20.00 | 20.00 | 20 |
| | Perfume Cotton Touch (=E)) | Parfum | 0.50 | 0.50 | 0.50 | 0.50 | 0.50 | 0.50 | 0.50 | 0.50 | 0.50 |
| | Sodium Chloride (=E)) | Sodium Chloride | 0.10 | 0.35 | 0.40 | 0.25 | 0.35 | 0.20 | 0.35 | 0.50 | 0.50 |
| | Citric Acid (50% solution) (=E)) | Citric Acid | 0.52 | 0.62 | 0.64 | 0.68 | 0.60 | 0.67 | 0.72 | 0.57 | 0.75 |
| | pH value (23° C.) | | 4.5-4.9 | 4.5-4.9 | 4.5-4.9 | 4.5-4.9 | 4.5-4.9 | 4.5-4.9 | 4.5-4.9 | 4.5-4.9 | 4.5-4.9 |
| | Storage stability (4 weeks at 40° C.) | | ++ | ++ | ++ | ++ | ++ | ++ | ++ | No (*) | No (**) |

++ means: stable; no separation;
No (*) = crystals and separation were formed after 2 weeks;
No (**) = separation after 1 week
Shower creams with concentrates according to Examples 1 show significantly higher storage stability than the shower cream with an anionic surfactant containing concentrate (comparison example 2) and a shower cream without a concentrate (comparison example 3).

The invention claimed is:

1. A concentrate for stabilizing a wax dispersion comprising waxes selected from the group consisting of a mono-and/or diester of mono-and/or diethylene glycol consisting of
    (a) hydrogenated castor oil, in an amount of 0.5 to 7% by weight based on the concentrate,
    (b) one or more amphoteric or zwitterionic surfactants selected from the group consisting of betaines in an amount of 30.0 to 40.0% by weight based on the concentrate,
    (c) 5.0 to 10.0% by weight of other auxiliaries or additives, and
    (d) add up to 100% by weight water.

2. The concentrate as claimed in claim 1, wherein a quantity ratio of betaine (b) to hydrogenated castor oil (a) is in a range from 2:1 to 15:1.

3. A concentrate for stabilizing a wax dispersion comprising waxes selected from the group consisting of a mono-and/or diester of mono-and/or diethylene glycol consisting of
    (a) 0.5 to 7.0% by weight of hydrogenated castor oil,
    (b) 10.0 to 35.0% by weight of amphoteric or zwitterionic surfactants selected from the group consisting of betaines, (c) 5.0 to 30.0% by weight of nonionic emulsifiers,
(d) 2.0 to 10.0% by weight of other auxiliaries or additives,
(e) and add up to 100% by weight by water.

4. The concentrate as claimed in claim 1 having a viscosity measured by Brookfield, VT; spindle 4; 10 rpm: 23° C. in the range of 8,000 to 25,000 mPas.

5. A process for the production of the concentrate claimed in claim 1, wherein the concentrate is prepared by mixing components (a), (b) and (d) together, adding the necessary quantity of water, heating the mixture to about 85 to 90° C., and cooling down with agitation.

6. A method of stabilizing a wax dispersion comprising waxes selected from the group consisting of mono-and/or diesters of mono-and/or diethylene glycol comprising the use of a concentrate as claimed in claim 1.

7. The method of claim 6, wherein the wax dispersion comprising waxes selected from the group consisting of mono-and/or diesters of diethylene glycol and a fatty acid mixture containing 85 to 100% by weight stearic acid and 0 to 15 wt % different fatty acids with 12 to 22 carbon atoms, based on fatty acid mixture.

8. The method as claimed in claim 6, wherein the wax dispersion comprising mono-and/or diesters of diethylene glycol has an average particle size, measured via laser diffraction, from 0.8 to 3.5 μm.

9. The method as claimed in claim 6, wherein the concentrate stabilizes a wax dispersion contained in personal care compositions as a pearlizing and/or opacifier agent.

10. A personal care composition comprising
  A) a concentrate as claimed in claim 1 and
  B) a wax dispersion comprising waxes selected from the group consisting of mono-and/or diesters of mono-and/or diethylene glycol
  C) one or more detersive surfactants selected from an anionic surfactant, an amphoteric surfactant, or a zwitterionic surfactant and
  D) an optional cationic polymer and
  E) optional other component(s) different from C) and/or D).

11. A process for the production of a personal care composition as claimed in claim 10, wherein one or more surfactant C) and the wax dispersion B) and optional cationic polymer D) are mixed at room temperature, and the concentrate A) are added and stirred together; wherein the optionally other components E) is added before or after the addition of the concentrate A).

12. The concentrate as claimed in claim 1, wherein the betaine is present in an amount of from 11 to 45% by weight, based on the concentrate.

13. The concentrate as claimed in claim 3 having a viscosity measured by Brookfield, VT; spindle 4; 10 rpm: 23° C. in the range of 8,000 to 25,000 mPas.

14. A process for the production of the concentrate claimed in claim 3, wherein the concentrate is prepared by mixing components (a), (b) and (d) together, adding the necessary quantity of water, heating the mixture to about 85 to 90° C., and cooling down with agitation.

15. A method of stabilizing a wax dispersion comprising waxes selected from the group consisting of mono-and/or diesters of mono-and/or diethylene glycol comprising the use of a concentrate as claimed in claim 3.

16. The method of claim 15, wherein the wax dispersion comprising waxes selected from the group consisting of mono-and/or diesters of diethylene glycol and a fatty acid mixture containing 85 to 100% by weight stearic acid and 0 to 15 wt % different fatty acids with 12 to 22 carbon atoms, based on fatty acid mixture.

17. The method as claimed in claim 15, wherein the wax dispersion comprising mono-and/or diesters of diethylene glycol has an average particle size, measured via laser diffraction, from 0.8 to 3.5 μm.

18. The method as claimed in claim 15, wherein the concentrate stabilizes a wax dispersion contained in personal care compositions as a pearlizing and/or opacifier agent.

19. A personal care composition comprising
  A) a concentrate as claimed in claim 9 and
  B) a wax dispersion comprising waxes selected from the group consisting of mono-and/or diesters of mono-and/or diethylene glycol
  C) one or more detersive surfactants selected from an anionic surfactant, an amphoteric surfactant, or a zwitterionic surfactant and
  D) an optional cationic polymer and
  E) optional other component(s) different from C) and/or D).

20. A process for the production of a personal care composition as claimed in claim 19, wherein one or more surfactant C) and the wax dispersion B) and optional cationic polymer D) are mixed at room temperature, and the concentrate A) are added and stirred together; wherein the optionally other components E) is added before or after the addition of the concentrate A).

* * * * *